United States Patent [19]

Roberts et al.

[11] Patent Number: 5,388,571
[45] Date of Patent: Feb. 14, 1995

[54] POSITIVE-PRESSURE VENTILATOR SYSTEM WITH CONTROLLED ACCESS FOR NEBULIZER COMPONENT SERVICING

[76] Inventors: Josephine A. Roberts, 7509 Ben Avon Rd., Bethesda, Md. 20817; Jephthae W. Burwell, 3119 Adams Mill Rd., NW., Washington, D.C. 20010

[21] Appl. No.: 988,031

[22] Filed: Dec. 9, 1992

Related U.S. Application Data

[63] Continuation of Ser. No. 653,075, Feb. 11, 1991, abandoned, which is a continuation-in-part of Ser. No. 349,216, May 9, 1989, Pat. No. 5,119,807, which is a continuation-in-part of Ser. No. 311,959, Feb. 17, 1989, abandoned, which is a continuation-in-part of Ser. No. 74,867, Jul. 17, 1987, Pat. No. 4,805,609.

[51] Int. Cl.$^6$ ............... A61M 15/00; A61M 16/10
[52] U.S. Cl. ............... 128/203.12; 128/205.12; 128/912; 128/200.18; 128/200.23; 128/200.21
[58] Field of Search ............... 128/200.14, 200.21, 128/200.22, 200.24, 203.12, 203.14, 203.19, 204.16, 204.18, 205.12, 205.24, 205.27, 912, 200.18, 200.23; 239/338, 343, 352, 370, 304, 320, 104, 124; 604/83, 85, 187, 218

[56] References Cited

U.S. PATENT DOCUMENTS

| | | | |
|---|---|---|---|
| 3,097,645 | 7/1963 | Lester. | |
| 4,279,250 | 7/1981 | Valenta et al. | 128/200.14 |
| 4,457,305 | 7/1984 | Shanks et al. | 128/205.12 |
| 4,703,753 | 11/1987 | Bordoni et al. | 128/200.14 |
| 4,805,609 | 2/1989 | Roberts et al. | 128/200.21 |
| 4,823,784 | 4/1989 | Bordoni et al. | 128/200.14 |
| 4,938,210 | 7/1990 | Shene et al. | 128/203.12 |

FOREIGN PATENT DOCUMENTS

| | | | |
|---|---|---|---|
| 3643624 | 8/1987 | Germany | 128/207.15 |
| 1488249 | 10/1977 | United Kingdom | 128/200.14 |

*Primary Examiner*—Kimberly L. Asher
*Attorney, Agent, or Firm*—John J. Byrne

[57] ABSTRACT

A nebulizer component, interconnected in the inspiratory flow path, includes an interior chamber with a lower region for storing liquid medicine at system pressures and an upper region containing a nebulizer (jet atomizer and baffle) for periodically nebulizing the liquid medicine for producing a fog of nebulized particles suspended in gas which mix with the breathable gas which flows through the chamber to the patient. Medical apparatus for removing any potentially contaminated residual medicine or condensed liquid from the lower region, for introducing liquid medicine for storage in the lower region for a subsequent nebulizer treatment, and for immediate introduction of nebulized liquid medicine during any bronchospasm crises are provided in order to maintain the pressures and function of the system, prevent the spread of contamination into the ventilator system or out of the system to attendants and others in the surrounding ambient environment, and eliminate sources of potentially life-threatening accidents during such removal and introduction. Specific embodiments include a novel liquid medicine vial, an adapter for a probe-activated valve, and specific arrangements of flow-paths, valves, and connectors to provide for maintaining pressures and function and for preventing spread of contamination during such removal and introductions for a ventilator system which is more economical and less labor intensive to operate.

12 Claims, 5 Drawing Sheets

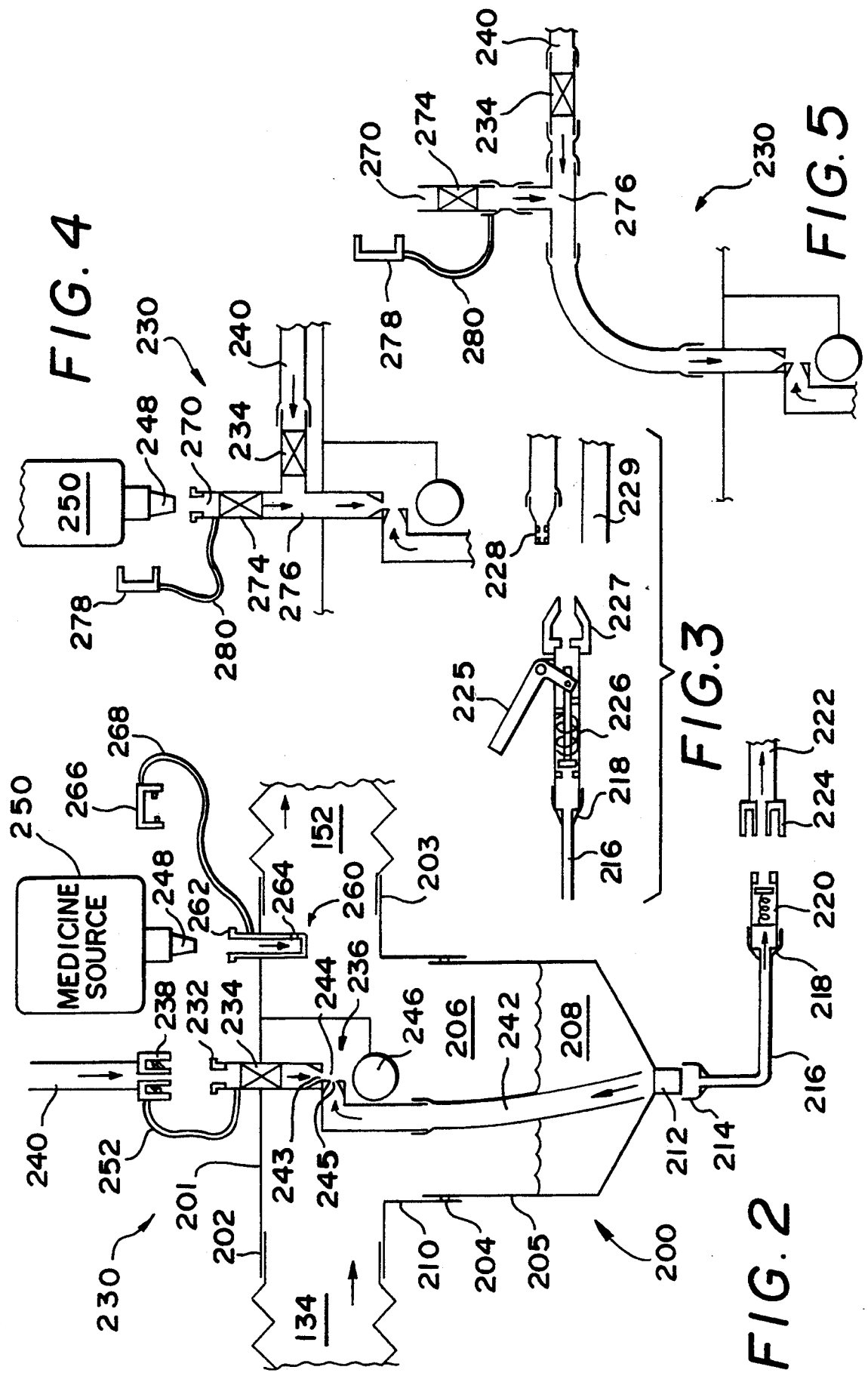

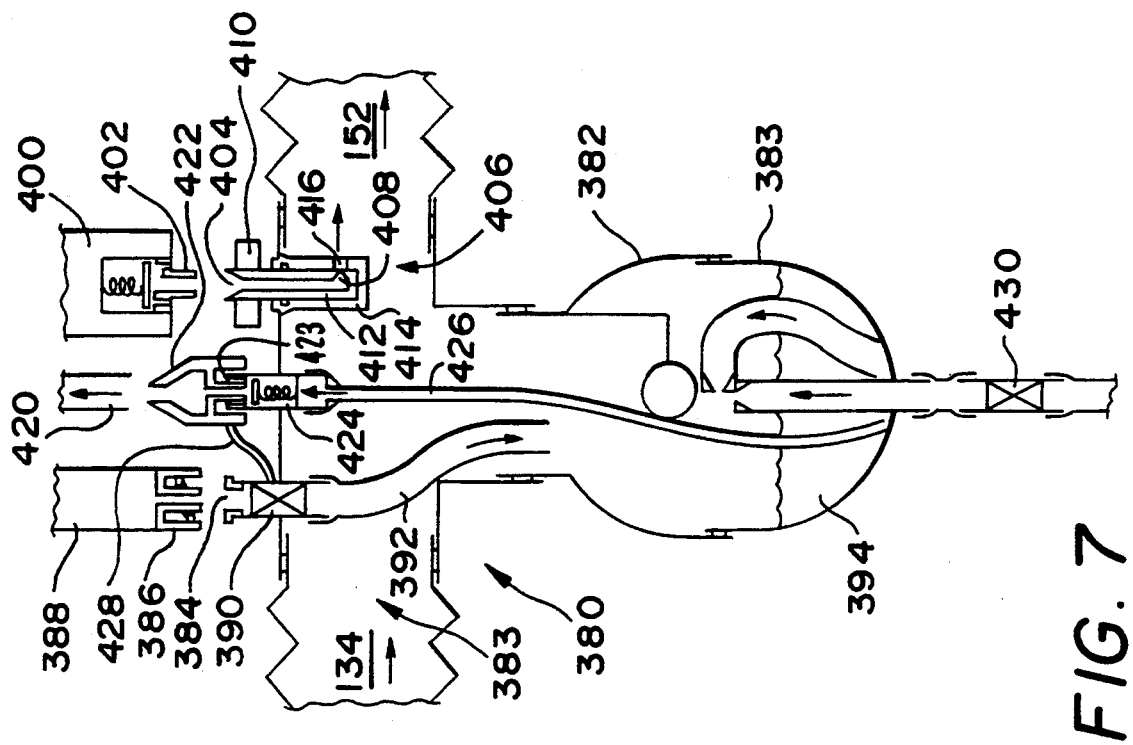
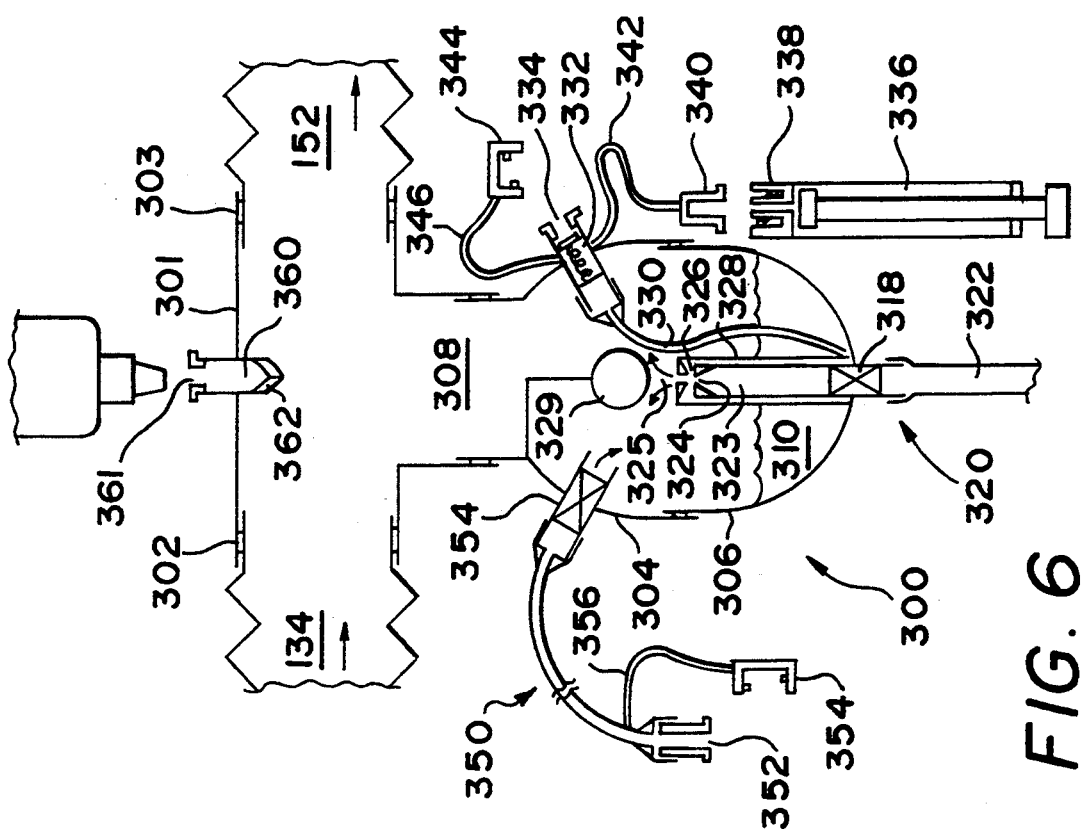

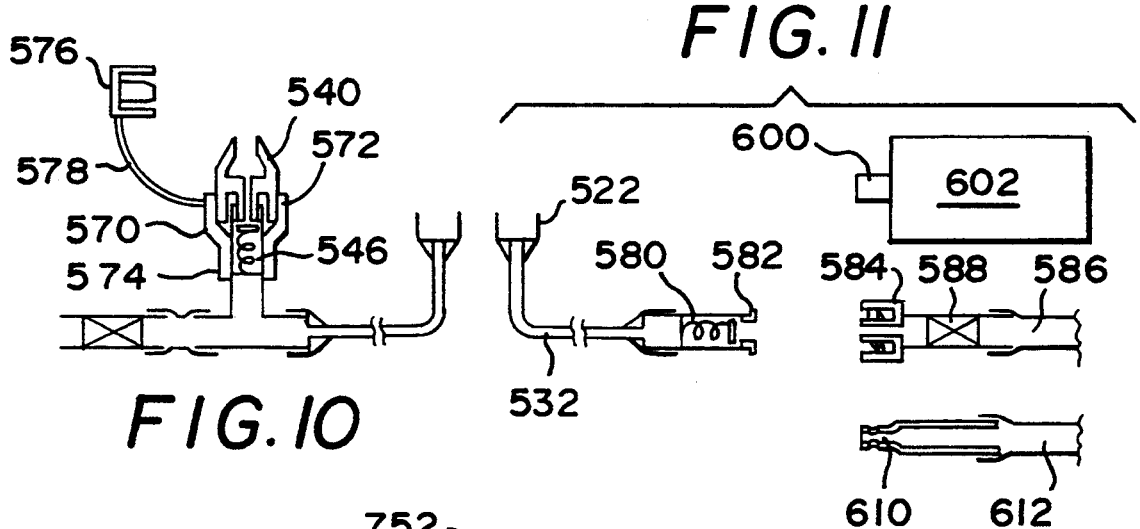
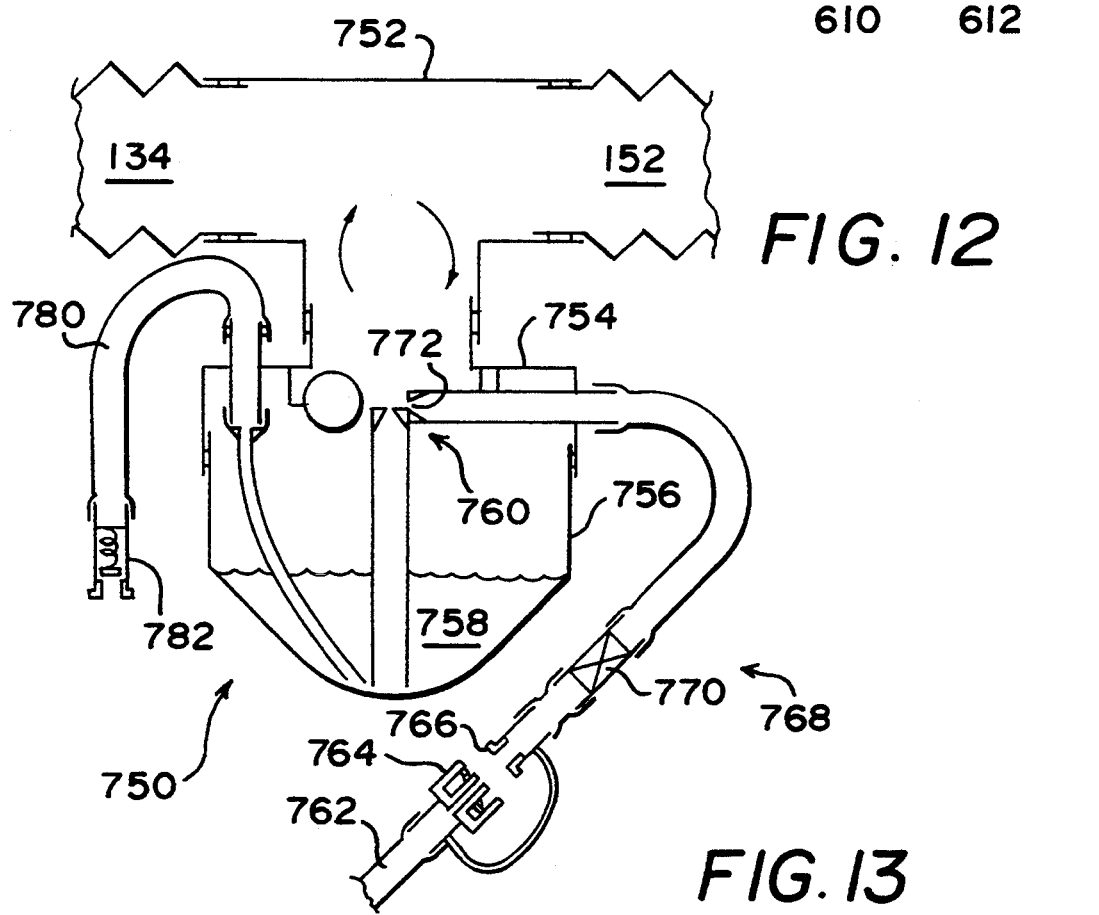

POSITIVE-PRESSURE VENTILATOR SYSTEM WITH CONTROLLED ACCESS FOR NEBULIZER COMPONENT SERVICING

This is a continuation, of application Ser. No. 07/653,075, filed Feb. 11, 1991, now abandoned; which was a continuation-in-part of application Ser. No. 07/349,216, entitled PRESSURIZED MEDICAL VENTILATION SYSTEM, filed May 9, 1989, now U.S. Pat. No. 5,119,807, which is a continuation-in-part of application Ser. No. 07/311,959, entitled PRESSURIZED VENTILATION APPARATUS FOR PATIENT, filed Feb. 17, 1989, now abandoned, which is a continuation-in-part of application Ser. No. 07/074,867, entitled PRESSURIZED VENTILATION SYSTEM FOR PATIENTS, filed Jul. 17, 1987, now U.S. Pat. No. 4,805,609, all of which are owned by a common assignee and the entire disclosures of which are incorporated herein by reference.

This application relates to a positive-pressure ventilator system which provides control and augmentation of breathing for a patient with respiratory insufficiency and which includes a nebulizer for delivering particles of liquid medication into the airways and alveoli of the lungs of a patient; and, more specifically, to methods and apparatus for removing undesired liquids from a nebulizer chamber within the system and for introducing liquid medication into the nebulizer chamber at system pressures to store the liquid medication and to nebulize the medication for such delivery into the lungs.

Patients in an intensive care unit, who are unable to maintain arterial blood-gas tensions and acid-base balance within safe ranges with their own breathing efforts and supplemental oxygen, have respiratory insufficiency and require mechanical ventilation of their lungs. Either a tracheotomy or an endotracheal breathing tube is positioned in the patient's main airway with an internal end positioned for exchange of gas within the lungs and an externally protruding end for connection with a ventilator system. A positive-pressure ventilator system, for providing heated, humidified, bacterially-filtered, breathable gas, such as oxygen-enriched air, is attached to the externally protruding end of the patient's breathing tube to supply mechanically-assisted repetitive respiration cycles. In each cycle, gas is pumped through the breathing tube into the lungs to ventilate the lungs, and then exhaled gas is allowed to flow out of the lungs.

In a typical positive-pressure ventilator system, a ventilator pumps a breathable gas in cycles of preset tidal volume or preset maximum pressure. Such cycles occur at a preset rate (respiration rate) and/or upon patient-initiation to provide prescribed ventilation of the patients lungs. The gas flows from the ventilator through a heated humidifier which warms and humidifies the gas to approximately 100% humidity at body temperature. The heated, humidified, breathable gas is directed through a main-conduit inspiratory flow-path of flexible hose with interconnected components to the patient breathing tube connection and into the lungs.

A nebulizer component, interconnected with the flexible hose of the inspiratory path, introduces nebulized particles of liquid medication, periodically as prescribed, into the breathable gas flowing through the inspiratory flow-path to the patient for delivering the particles of liquid medication into the airways and alveoli of the lungs.

A wye adaptor connects the external end of the breathing tube with both the inspiratory and expiratory flow-paths of the main-conduit. Exhaled gas from the lungs is directed through an expiratory limb of the wye adaptor through a flexible hose, past an open exhalation valve, and out of the system through an exhalation port. The port is positioned and/or the exhaled gas is filtered in such a way as to minimize contamination of attendants and patients in the surrounding ambient environment.

Ventilator systems are hermetically-sealed by tight-fitting connections between the ventilator components, by the closing of the exhalation valve and by a seal between the breathing tube and patient's trachea. For adult patients, the seal between the breathing tube and the trachea is usually provided by a cuff attached near the internal end of the breathing tube which is inflated to seal; for others, the diameter of the breathing tube is selected for providing such sealing.

At a preset time, or upon patient-initiation, an inspiratory phase of a respiratory cycle begins. The ventilator closes the exhalation valve and pumps gas into the system which increases the system pressure in the range of 20 to 100 cm $H_2O$, approximately, to inflate the lungs. After a preset tidal volume or preset pressure is reached the ventilator stops pumping.

After the inspiratory phase, the expiratory phase of the respiratory cycle begins. The ventilator opens the exhalation valve which allows the lungs to recoil and exhaled gas to flow out past the open exhalation valve, through the exhalation port and into the surrounding ambient environment. The ventilator system may also include a threshold or flow resistor to provide positive end expiratory pressure (PEEP) (between 2 and 20 cm $H_2O$).

The nebulizer component includes a chamber with a lower cup-like section for storing a dose of liquid medicine and one or more upper sections which enclose a fog of liquid particles, suspended in breathable gas, which mixes with the breathable gas flowing through the main-conduit inspiratory path to the patient. The nebulizer chamber also encloses a nebulizer (jet atomizer and baffle) to nebulize the medicinal liquid stored in the lower section for producing such fog. Nebulizing-gas, usually supplied from the ventilator, is directed through a small-bore flexible tube to the nebulizer to produce the fog of gas and liquid medication particles of a size selected for depositing in the airways and alveoli of the lungs (2 to 4 microns) with minimum fall-out and evaporation.

Residual liquid medication and/or liquid formed by condensation in the nebulizer chamber can become contaminated between periodic nebulizer treatments. The potentially contaminated liquid must be removed from the positive-pressure system before adding a dose of liquid medicine for the next nebulizer treatment in order to prevent introduction of contaminated liquid into the patient's lungs. The lower cup-like section of common nebulizer components may be unscrewed and detached for dumping contaminated liquids out of the cup and measuring liquid medication into the cup and then the cup-like section reattached for nebulizer treatments.

Nebulized particles of liquid medicine may also be introduced directly into the system when mechanically ventilated patients experience unexpected bronchial spasms which interfere with prescribed breathing. In such situations, the ventilator system may be opened and nebulized particles of liquid medication introduced from a pressurized canister into the patient breathing tube. Then the system is re-closed and mechanical ventilation resumes.

It is the object of this invention to provide a ventilator system which may be continuously operated without loss of system pressures or function during the periodic introduction of medicinal liquids into the nebulizer chamber and/or periodic removal of potentially contaminated liquid from the nebulizer chamber. Another object is to provide for such introduction and/or removal without spreading contamination into the system or out of the system potentially exposing attendants and others in the surrounding ambient environment. Another object of the invention is to eliminate sources of accidents which could result in contamination or prolonged loss of system pressure and/or function. Another object is to provide a ventilator system which is more economical and less labor-intensive to operate.

These and other objectives of the invention, along with advantages and features of specific embodiments, are described along with the accompanying drawings in which:

BRIEF DESCRIPTION OF THE DRAWINGS

FIG. 2 schematically illustrates a specific embodiment of the nebulizer component of the invention illustrating means for periodically introducing and storing a dose of liquid medication in the nebulizer chamber, means for periodically removing contaminated liquid from the nebulizer chamber and means for introducing nebulized liquid medicine from a pressurized canister into the nebulizer chamber;

FIG. 3 schematically illustrates another embodiment of the means for periodically removing contaminated liquid of FIG. 2 using a lever-activated valve in removal path means;

FIG. 4 schematically illustrates an alternate embodiment of means for introducing and storing liquid medicine of FIG. 2 using a branch adaptor at the nebulizing-gas port of the nebulizer component;

FIG. 5 schematically illustrates another embodiment of means for introducing and storing liquid medicine of FIG. 2 using a branch component interconnected within the nebulizing-gas flow-pathway;

FIG. 6 schematically illustrates a specific updraft nebulizer component embodiment of the invention showing access means for periodically introducing and storing liquid medication, access means for periodically removing contaminated liquid, access means for introducing nebulized liquid from a pressurized canister into the nebulizer component and means for preventing leakage of liquid down the nebulizing-gas flow-pathway;

FIG. 7 schematically illustrates a hollow T-piece section embodiment of the invention with horizontally-oriented inlet and outlet arms having ports with connections for interconnection with the main conduit, a bottom port with connection for attaching a hollow bottom section to form an updraft nebulizer component, and access means through the top of the T-piece for servicing the nebulizer component;

FIG. 9 schematically illustrates another specific embodiment of the medical apparatus which provides access for adding medical liquid through the top of a T-piece section, and access for removing undesired liquid and introducing nebulizing-gas through the nebulizing-gas nipple at the bottom of the nebulizer chamber;

FIG. 10 schematically illustrates another specific embodiment of the medical apparatus of FIG. 9 in which a sealing sleeve connects between a probe-activated valve and a probe-adaptor.

FIG. 11 schematically illustrates another embodiment of the medical apparatus in which a probe-activated valve provides for selectively attaching-/detaching liquid disposal means, liquid medicine source means, or nebulizing-gas source means, alternately as required, for servicing the nebulizer component.

FIG. 12 schematically illustrates a specific embodiment of a side-stream nebulizer component of the invention which provides controlled access for adding medicinal liquid into the chamber through the nebulizing-gas flow-pathway and for removing liquid from the lower-region of the nebulizer chamber;

FIG. 13 shows a partial section of a probe-adaptor of the invention which permits either a suction tube or a hollow suction probe to seal with the adaptor for fluid communication through a valve that opens only when force is being applied by a probe to activate the valve.

DETAILED DESCRIPTION OF THE PREFERRED EMBODIMENTS

The invention of the application includes recognition of limitations of prior ventilator systems which have not been previously identified in the art and includes analysis of methods and apparatus for solving problems which have been unsolved for decades.

In the invention, novel access means provide for control of fluid movement from the surrounding ambient environment into the system nebulizer chamber at system pressures, and fluid movement from the nebulizer chamber out of the system without altering the pressures or function of the system or exposing the operator/attendant to contaminated fluid, or the patient to contamination from the surrounding ambient environment.

In a specific embodiment of the invention, hermetically-sealed ventilator system 100 of FIG. 1 provides prescribed control and augmentation of patient breathing. The ventilator system provides repetitive breathing cycles by increasing the system pressure to inflate the lungs during an inspiratory phase and then opening an expiration valve to allow system pressure to decrease and the lungs to deflate during an expiratory phase for each cycle.

The inspiratory phase for each cycle is commonly initiated at a preset time and/or triggered by the patient. During inspiration, ventilator 102 pumps filtered, breathable gas as required for the ventilator system. The gas is directed through conduit 104 and through heater/humidifier 106 to provide approximate body temperature and 100% relative humidity for the inspired gas. Then the gas flows into a ventilator/patient circuit of flexible hose with various components serially interconnected therein.

Figure 1:
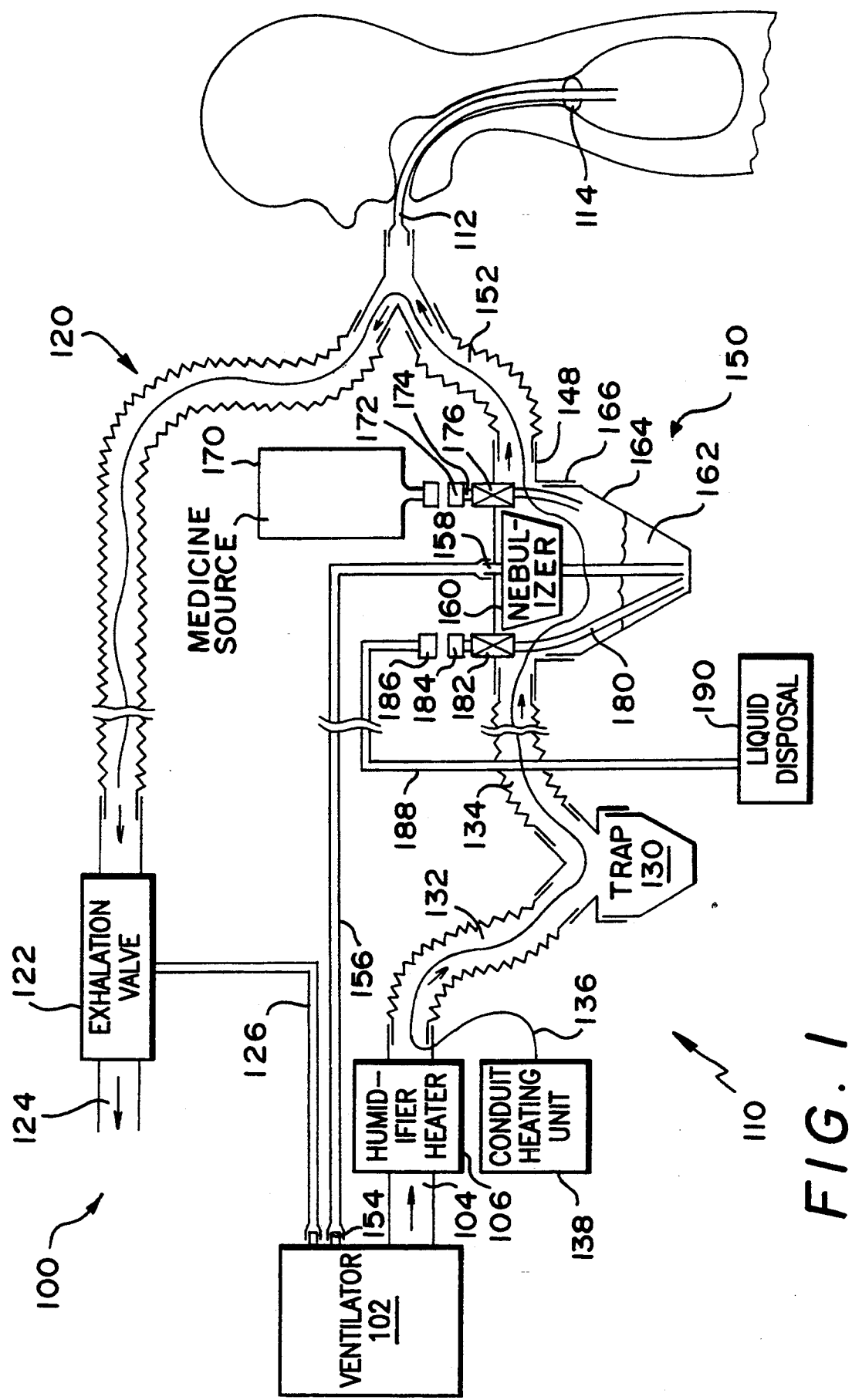
FIG. 1 schematically illustrates a ventilator system of the invention showing a ventilator circuit of flexible hose and components interconnected therein and extending from the ventilator and humidifier to a connection with a patient's endotracheal tube and through an exhalation port.

The gas flows through an inspiratory flow-path 110 of the ventilator circuit into the external, protruding end of a patient breathing tube 112. The breathing tube may be an endotracheal tube inserted through the nose or mouth or a tracheotomy tube inserted through a surgical aperture in the patient's trachea. The tube is routed through the patient's airway into the lungs and secured in the patient's airway by means of an inflatable balloon cuff 114 that holds the breathing tube in apposition with the airway wall and hermetically seals to prevent the pressurized breathable gas that is being pumped into the lungs from leaking out around the breathing tube.

The increased circuit pressure inflates the lungs of the patient. When the preset tidal volume of breathable gas has been pumped into the lungs or a preset inflation pressure achieved, the ventilator stops pumping the gas, and an exhalation valve opens to initiate the expiratory phase of the breathing cycle.

During the expiratory phase, elastic recoil of the patient's lungs occurs and the gas flows from the lungs through the breathing tube 112, through expiratory flow-path 120 of the circuit, past open exhalation valve 122 and out exhalation port 124 into the surrounding environment. The ventilator controls the timing of inspiration and expiration by signals through control path 126 to control opening/closing of the exhalation valve. For example, the exhalation valve may be a mushroom-type valve that is inflated on inspiration by a flow of pressurized gas supplied through path 126 to close the circuit to the atmosphere. At the end of inspiration the mushroom balloon deflates and exhalation occurs.

As the breathable gas flows from the humidifier to the patient breathing tube, the gas may cool causing some of the water vapor to condense and form liquid within the flexible hose and within the interconnected components. Water traps for collection of condensate by gravity from the flexible hose segments may be interconnected in the expiratory flow-path and/or interconnected in the inspiratory flow-path before and/or after the nebulizer. Water trap 130 is shown interconnected within inspiratory flow-path 110 positioned before the nebulizer component in the direction of flow between flexible hose segments 132,134. Conduit heating means may be provided to maintain constant temperature for gas flowing through the circuit. Thermistor and heating wires 136, attached to conduit heating unit 138, enter the ventilator circuit at the humidifier and are routed through the length of the patient's circuit to exhalation valve 122. The humidifier and conduit heating unit may be one integral unit or separate as shown to provide electrical power to the wires, and the thermistor wire an/or heating unit control such conduit heating. Use of a heated wire reduces condensation in the flexible hose which may eliminate the need for water trap 130 and also reduces the accumulation of condensate in the interconnected components.

Hollow T-piece section 148 of nebulizer component 150 is interconnected within inspiratory flow-path 110 of the circuit between flexible hoses 134,152 for introducing nebulized particles of liquid medicine into the gas flowing through the inspiration path to the patient. When a nebulizing switch (not shown) of the ventilator is turned on, the ventilator provides nebulizing-gas from ventilator connection 154 through nebulizing-gas tube 156 through nebulizing-gas port 158 into the nebulizer component to nebulizer 160 in order to nebulize a dose of liquid medicine 162 stored in the bottom cup-like section 164 of the nebulizer component for producing such liquid particles. In a volume-controlled embodiment, the ventilator supplies the same selected tidal volume of gas to the patient whether nebulizing-gas is supplied to the nebulizer or not.

Liquids must be periodically removed from the interior chamber of the nebulizer component. Undesired liquids, such as accumulated condensate and residual liquid medicine remaining after previous nebulizer treatments, may become contaminated after a relatively short period. There is a possibility that contaminated liquid in cup-like bottom section 164 may be spilled into the inspiratory flow-path and be conveyed into the patient's lungs. For each nebulizer treatment, any remaining liquid must be extracted from the system before inserting a dose of liquid medicine into the chamber so as to prevent nebulizing contaminated liquid into the patient's lungs.

Previously, the cup-like bottom section 164 was periodically detached at a threaded or sliding-sleeve, force-fit connection 166 for transferring undesired liquids out of and/or depositing a dose of liquid medication into the bottom section before each nebulizer treatment. Removing the nebulizer cup to service the nebulizer can seriously compromise the patient's respiratory status by interrupting the ventilation support for the patient, exposing the system to contamination from the surrounding ambient environment and spreading infection to attendants and other patients in such environment. Even short periods of lost support may seriously compromise the stability of critical patients.

Previously, during such servicing, contamination could spread, as moisture was sprayed in the face and on the hands of the attendant by the sudden rush of compensatory pressure at the time of detachment of the nebulizer cup. Contamination of the system could occur due to airborne contaminants entering the system; or, if the attendant inadvertently touched the interior or lip of the cup or other exposed interior section of the nebulizer chamber. Such cross-contamination was a common concern as attendants went from patient to patient servicing nebulizer components.

Such servicing of the nebulizer component previously required special knowledge, skill and attention to detail on the part of the attendant to open the system, empty the accumulated moisture, add the medication, and quickly reseal the system. Mishaps were difficult to avoid, considering the complexity of the servicing task performed under time constraints. If the nebulizer chamber was not carefully reattached, continuous leakage of pressure could reduce tidal volumes below prescribed levels, possibly without any warning. Medication or contaminated fluid could also leak out of the nebulizer component into the surrounding environment. This was a particular problem with the disposable-type nebulizers commonly used.

In previous nebulizer components, the cup-like bottom section 164 could accidentally fall off the T-piece section 148, due to improper reattachment, repeated servicing, patient movement and system vibrations. The bottom section could drop onto the floor, interrupting ventilation and spreading contamination into and out of the system.

In the nebulizer component of the invention, the cup-like bottom section 164 is not removed for servicing and preferably, connection 166 is permanently bonded or of one-piece construction to prevent such problems. Medical apparatus for servicing the nebulizer component are provided for removing undesired liquids and for adding liquid medication into bottom section 162 for nebulizer treatments.

Source of liquid medicine 170 may be attached at connection means 172 for periodically introducing a dose of liquid medicine through introduction path means 174, such as a small-bore flexible plastic tube, past valve means 176 and into the system to store liquid medicine in bottom section 164 for the subsequent nebulizer treatment. The source 170 must provide for pressurizing the medicine sufficiently to force the fluid past valve means 176 into the nebulizer chamber. The connection means and valve means are selected to enable such pressurized introduction of medical liquids, while maintaining the pressures and function of the system and preventing spread of contamination from the surrounding environment into the system or spread of contamination from the system to the attendant or other patients in the surrounding environment.

Common sources of liquid medicine include syringes filled with medicine, unit-dose vials and metered-dose vials. Flexible plastic unit-dose vials may be connected, with the vial exit oriented downward, through a valve for bidirectional fluid communication with the nebulizer chamber which allows the pressure fluctuations of the system to discharge the liquid; otherwise, such plastic unit-dose vials are squeezed by the attendant for discharging into the chamber at system pressures. A canister-type, metered-dose vial for immediate introduction of nebulized particles during a bronchial spasm emergency is usually provided with sufficient internal pressure to nebulize the liquid medicine during introduction.

For introducing liquid medicine for storage in lower region 162, valve means 176 may include two-way valve means for bidirectional flow through the fluid path past the valve. Such two-way valve means include stop-cock, gate, globe, diaphragm, or similar valves which must be manually opened and manually closed; push-button, lever-activated or tube-clamp valves which move a barrier to unblock flow only when an attendant is applying force to activate the valve and automatically block flow at other times; or probe-activated valves which automatically move a barrier to unblock fluid flow only when a hollow activating-probe, for fluid communication, is inserted into the valve and otherwise automatically move the barrier to block flow. Preferably, such valve means include one-way valve means for providing only unidirectional flow into the nebulizer chamber. Such one-way valve means include duck-bill, diaphragm or spring-activated check valves which automatically move a barrier to unblock fluid flow, when sufficient pressure is applied for introducing fluids into the nebulizer chamber and otherwise automatically move the barrier to block fluid flow.

For introducing nebulized particles of liquid medicine from a pressurized canister, valve means 176 may include such unidirectional or bidirectional valve, or a pinhole jet nozzle restriction in conjunction with a cap for blocking introduction path means when not in use.

The selection of such valve means based on this disclosure is within the ability of those skilled in the art without undue experimentation, but valve means 176 of this invention also includes any means to control flow by moving a barrier for blocking and unblocking the fluid flow through path means to allow attachment and detachment of liquid medicine source means and detachment controlled introduction of liquid medicine while maintaining the pressures and function of the ventilator system and preventing the spread of contamination.

Connection means 172 may include, for example, a luer-lock threaded connector, a connector similar to a luer-lock but without threads, a rounded, rigid nipple onto the exterior of which the end of a flexible tube is forced to slide in the axial direction, a rounded aperture into which a probe is forced to slide, or the connection between the source and the external end of path means can be sealed by constant force/pressure, applied by the attendant, between complementary connectors of the source and path means.

Such connection means are well known in the art, but the connection means 172 of this invention include any means which could be used for sealed attachment and detachment of source means for medical liquid for introduction past such valve means while preventing the spread of contamination.

Undesired liquids are periodically removed from the bottom section of the nebulizer component through path means 180, such as a small-bore, flexible, plastic tube. Undesired liquid flows from the bottom of lower region 162 through path means 180, past valve means 182, through connection means 184, and into disposal means 186, 188, 190 for liquids. Valve means 182 and connection means 184 are selected to enable removal of contaminated liquids while maintaining the pressures and function of the system and preventing spread of contamination into the system or into the surrounding environment.

Valve means 182 may include valve means for bidirectional flow, previously discussed, or other means for controlling flow by moving a barrier for blocking and unblocking the liquid path means to allow controlled removal of undesired liquid through such path means.

Connection means 184 may include previously discussed connection means or other means for sealed attachment of disposal means for removal of liquid from the bottom section of the nebulizer component past such valve means while preventing the spread of contamination.

Disposal means 190 for liquid may include a hospital sanitary suction drain system, a collection container communicating with a source of vacuum or other liquid disposal vacuum source known in the art, a syringe for withdrawing liquid, or other evacuation means. Embodiments which provide for removing undesired liquid through the bottom of the nebulizer chamber may utilize a simple gravity drain system, such as a collection bag, for safe disposal of liquid.

Providing both means to add liquid medicine into the nebulizer component and means to remove undesired liquids eliminates the need to open the circuit. Thus, the nebulizer component can be sealed shut, eliminating sources of accidental circuit openings and sources of continuous leaks which may be life-threatening. Undesired liquid is removed and liquid medicines are added without the cross-contamination inherent in previous circuits. The nebulizer component servicing task is simpler and more safely accomplished, reducing the skill and labor required for periodic servicing. In a respiratory emergency nebulized medicine can be introduced immediately into the circuit; and the dangers inherent in opening the circuit during such emergencies can be eliminated.

Nebulizer component 200 in FIG. 2 includes a T-piece section 201 having an inlet port with connection 202 and an exit port with connection 203 which are forced-fit, sliding sleeve connectors and which provide for interconnection within the inspiratory flow-path between flexible hose segments 134,152 respectively. Section 201 also includes a bottom port with connection 204 for sliding forced-fit or threaded attachment of cup-like bottom section 205. The bottom section is attached to the T-piece section to form an enclosed nebulizer chamber having upper region 206 and a lower region 208. In the upper region, breathable gas flowing through the conduit mixes with a fog of gas and nebulized particles. In the lower region, liquid medicine is stored for the nebulizer to produce such fog of gas and nebulized particles. Residual medicine and accumulated condensate must be removed from the lower region before introducing a dose of liquid medicine for such nebulizer treatment. Preferably, the cup-like bottom section is permanently bonded to the T-piece at connection 204 to prevent accidental detachment.

Medical apparatus for servicing the nebulizer component includes a liquid removal path means. Undesired liquid exits from lower region 208 through bottom nipple 212, through adaptor connection 214 which is forced to slide onto the nipple, through tube 216, through adaptor connection 218 which is forced to slide over the end of probe-activated valve 220, and then past the valve, into disposal means 222 for liquid which includes an activating-probe connector 224. Connector 224 is similar to a male luer-lock connector but with slightly smaller probe diameter and without threads for periodically attaching with a free-sliding fit to seal with and unblock valve 220. In this arrangement some liquid medicine will undesirably work its way down removal path means, thus the volume of liquid removal path means, is preferably as small as practical. Preferably, the path is as short as convenient access allows and tube 216 is micro-tubing. More preferably, tube 216 is eliminated and valve 220 is integrally connected at the bottom of the nebulizer component.

Valve 220 is preferably probe-activated, as shown, in order to automatically activate to unblock removal path means upon attachment to an activating-probe of removal means. Alternatively, another type of valve could be selected. For example, in FIG. 3 a lever-activated valve 226 is shown attached to the end of micro-tube 216 at connector 218. Lever-activated, push-button and tube clamp valves move a barrier into position to unblock the flow through path means only while the attendant is applying force/pressure to activate the valve. When the attendant stops applying force the barrier is automatically moved into position to block flow. When connected to the external end of removal path means, such valves provide for convenient periodic operation while applying pressure/force to seal with removal means. Tapered adaptor end 227 of valve 226 provides for attachment to either a probe 228, which is inserted into the adaptor or to a flexible end of a tube 229 which is forced to slide over the tapered exterior of the adaptor.

Once the undesired liquid is removed, liquid medicine may be introduced past valve 220 of FIG. 2 for storage in the cup-like bottom section for a subsequent nebulizer treatment. However, residual medicine would remain in removal path means, and access through the top of the nebulizer component T-piece section provides more convenient introduction of medicine.

Medical apparatus may include shared flow-path 230 which directs fluids through female luer-lock connector 232, past one-way valve 234 and into nebulizer 236. The shared flow-path may be attached to male luer-lock connector 238 of tube 240 of means for supplying nebulizing-gas.

Vacuum pathway means 242, such as an aspirator tube, extends from the bottom of the lower region up to the nebulizer 236 positioned within the nebulizer chamber. When nebulizing-gas is flowing through the shared flow-path, nozzle means 243, such as a Din-hole at the end of the shared flow-path, produce a jet of gas at 244. The jet is directed across a small opening, such as pinhole orifice 245 which pierces through the upper end of vacuum tube means 242. The jet interacts with the hole to create a vacuum at the small opening hole 245. The vacuum draws liquid medicine, stored in the lower region, up through vacuum pathway means and through the orifice. The jet interacts with the liquid to break the liquid into small particles which are entrained in the jet. The jet directs the particles toward baffle 246. The small particles travel around the baffle and the larger particles impact the baffle to fall back into the lower region. The configuration of the jet atomizer and baffle are selected to produce the desired particle size for reaching the airways and alveoli of the lungs and for depositing the particles therein. Such particles become suspended in the gas inside the nebulizer chamber upper region to produce a fog which mixes with the breathable gas flowing to the patient.

The nebulizing-gas source may be detached from the shared flow-path 230, as shown in FIG. 2, for inserting male, convex, tapered tip 248 of source container 250 of liquid medicine into the female luer-lock connector 232. The tip and the rounded internal surface of the connection means co-operate to provide sealed attachment for introducing liquid medicine into the nebulizer chamber through shared flow-path 230.

An elongated, string-like, flexible holder 252 is connected between the nebulizing-gas source tube connector 238 and shared flow-path connector 232. The elongated holder positions the end of the nebulizing-gas tube in the proximity of the external end of the shared flow-path when they are detached to provide convenient reattachment, and to prevent the nebulizing-gas source tube from accidentally dropping.

Occasionally, patients dependent upon a ventilator system experience unexpected bronchial spasms which interfere with breathing. During such respiratory crises, previous ventilator circuits were opened, and nebulized liquid medicine was sprayed into the patient breathing tube from a pressurized canister. For example, Nowacki et. al. U.S. Pat. No. 4,470,412. Opening the circuit resulted in cross-contamination and further interfered with ventilation at a time when ventilation had been insufficient. Accidents, such as inadvertent repositioning of the patient's breathing tube, system leaks at the wye connector or other part of circuit, or dropping such pieces, could result.

Recently it has been proposed to add an additional component to the ventilator circuit for such introduction of nebulized liquid from pressurized canisters. For example, Shene U.S. Pat. No. 4,938,210 incorporated herein by reference.

The invention eliminates the need for additional circuit components. Access means of the invention may be selected to provide for immediate introduction of nebulized fluid from a pressurized canister into the nebulizer chamber during bronchospasm without opening the circuit. Thus the delay required to open the system, and disadvantages inherent in altering the system pressures and interrupting ventilation, are eliminated while preventing life-threatening accidents and cross-contamination.

Medicine source 250, as previously discussed, may be any means capable of attaching and sealing with the external end of the shared flow-path and providing pressurized liquid medicine. For example, a canister may be provided having sufficient internal pressure to nebulize the liquid as it exits the tip of container 250 or as the liquid flows as a jet out of nozzle means 244. Any medication which is not effectively nebulized by the internal pressure of the canister is deposited in the lower region 208 and is nebulized, using nebulizing-gas as previously described.

Path means 260 may be provided for immediate introduction of nebulized liquid medicine from a pressurized canister without detaching the nebulizing-gas flow-pathway. Tip 248 of source container 250 is inserted in a female luer-lock connector 262 and the liquid medicine flows through jet nozzle 264. For immediate introduction the pressure within container 250 should be sufficient to nebulize the liquid during introduction into the nebulizer chamber. The fog of particles of liquid medicine suspended in gas is sprayed out through the port of the horizontal arm of the nebulizer component T-piece and down the inspiratory flow-path in a jet toward the patient.

When path means 260 is not being used, male luer-lock cap 266 is attached to block the flow through path means to prevent leakage and contamination. The cap is attached to the nebulizer component by an elongated flexible holder 268. When a pressurized canister is attached at connector 262, the holder positions the cap near the connector for convenient, subsequent reattachment of the cap.

Alternate embodiments of the shared flow-path 230 are presented in FIGS. 3 and 4. A flexible end of nebulizing-gas supply tube 240 is forced over an end of one-way valve 234 of the shared flow-path. Tip 248 of liquid medicine source 250 may be inserted into connector 270 of the liquid introduction path means. Liquid medicine flows from container 250 past one-way valve 274 and into the shared flow-path at branch 276.

Connector 270 is covered by cap 278 when medicine is not being introduced, to minimize leakage and contamination. For convenient operation, elongated flexible holder 280 positions the cap in the proximity of connector 270 while source means is attached to connector 270.

In the type of nebulizer known as an "updraft nebulizer," the nebulizing-gas enters the nebulizer component through a flow-pathway which directs the gas upward through the bottom of the nebulizer component. Updraft nebulizer 300 in FIG. 6 includes a hollow T-piece section 301 with a horizontal inlet arm, terminating at a port with connection means 302 and a horizontal outlet arm, terminating at a port with connection means 303 for interconnection within the inspiratory flow-path between flexible hose segments 134 and 152 respectively. The bottom port of the T-piece upper section attaches to intermediate cylindrical section 304 which attaches to a bottom cup-like section 306. The three attached sections 301, 304, 306 form an enclosing nebulizer chamber. In upper region 308 of the chamber, gas flowing through the inspiratory flow-path mixes with a fog of nebulized liquid particles suspended in gas. In lower region 310 of the chamber, liquid medicine is introduced and stored for subsequent nebulizer treatment. Cup-like bottom section 306 may be attached with intermediate upper section 304 utilizing threads, and section 304 attached with T-piece section 302 using a sliding-sleeve, forced-fit connection, but preferably in the nebulizing component of this invention the sections are permanently bonded to prevent separation, and more preferably the three sections are of one-piece construction.

Previously, when the nebulizing-gas supply to an updraft nebulizer was turned off, pressures cycles drew residual medicine and/or accumulating condensate in the cup-like lower section up the vacuum pathway means and out of the nebulizer into the nebulizing-gas flow-pathway. When the nebulizing-gas was turned on for the next nebulizer treatment, the undesired liquid in the nebulizing-gas flow-pathway was forced back into the nebulizer component thus introducing potentially contaminated, nebulized liquid into the lungs of the patient.

In order to eliminate such contamination hazards, the medical apparatus for servicing the nebulizer component includes one-way valve 318 communicating with the nebulizing-gas flow-pathway 320 to prevent liquid in lower region 310 from working its way down the nebulizing-gas flow-pathway when the nebulizing-gas is turned off. Tube 322 of the source of nebulizing-gas is attached to valve 318, for example, by forcing an end of the tube to slide over an end of the valve.

Nebulizing-gas flows from tube 322 of a nebulizing-gas source, past valve 318, through innermost tube 323 of two concentric tubes, through nozzle means 324 and out of the top end of the innermost tube as a jet of nebulizing-gas at 325. The jet at 325 is directed across a small opening 326 between the top of innermost tube 323 and top of the outermost tube 328, then passes through an aperture in the top of the outermost tube, and is directed toward baffle 329. Liquid is drawn up through vacuum pathway means between innermost tube 323 and outermost tube 328 by a vacuum created as the jet is directed across the small opening 326. The jet breaks the liquid into a mixture of large and small particles of liquid medicine which are drawn into the jet and directed toward baffle 329. The larger particles impact against the baffle and either shatter into very fine particles or deposit onto the baffle and drip down into the lower region. The configuration of the jet nozzle and baffle are selected to provide particles of a size for conveyance, with minimum fallout and evaporation, through the inspiratory flow-path, through the breathing tube and into the airway and alveoli of the lungs, and for deposition in the airways and alveoli. The resulting particles are suspended in the gas within the upper region 308 for mixing with the breathable gas flowing through the inspiratory flow-path to the patient.

Valve 318 may also be used for controlled introduction of nebulizing-gas flow-pathway 320. Tube 322 may be detached from valve 318, and a source of liquid medicine (not shown) may be attached to valve 318 for introducing medicine into the nebulizing-gas flow-pathway. Subsequently, the nebulizing-gas source tube 322 is reattached and the nebulizing-gas is turned on which forces any liquid medicine remaining in the nebulizing-gas flow-pathway to flow into the nebulizer chamber for depositing the liquid in the lower region.

Undesired liquids are removed through tube 330, probe-activated valve 332, and female luer-lock connector 334. Disposal means for liquid, such as luer-lock syringe 336, are attached to seal with luer-lock connector 334 to remove and safely dispose of the undesired liquid. When liquid is not being removed, the male luer-lock connector 338 of liquid disposal means is attached to cap 340, which is positioned in proximity with connector 334 by elongated holder 342.

Cap 344 is attached to connector 334 to block removal path means when undesired liquid is not being removed, to eliminate any leakage past valve 332 and prevent spread of contamination. During removal of undesired liquid, the cap is positioned proximate to connector 334 by elongated holder 346 for convenient reattachment after such liquid removal.

A source of medicinal liquid which includes an activating-probe may be periodically attached to seal with connector 334 for periodically introducing a dose of medicinal liquid into lower region 310, past valve 332 and through tube 330.

Alternatively, path means 350 may be provided for periodically introducing a dose of liquid medicine into the chamber. A source of liquid medicine (not shown) such as a luer-lock syringe may be attached and sealed with female luer-lock connector 352, and liquid introduced past one-way valve 354, into lower region 310 for storage.

Cap 354 is attached to the external end of the path means at connector 352 to block introduction path means when liquid medicine source means is not attached, in order to eliminate any leakage past valve 354 and to prevent contaminants from entering introduction path means 350. The cap is positioned proximate to connector 352 by elongated holder 356 during such introduction to provide for sanitary storage and convenient reattachment of the cap.

Liquid medicine from a pressurized canister 358 may be introduced through path means 360. The canister is attached to connector 361 and liquid flows past one-way, duck-bill, check valve 362 and exits into the chamber as nebulized particles of liquid medication. Preferably, the mist is directed toward the patient as shown in later figures. A cap (not shown) may be provided as previously described for path means 350.

The horizontal arms of T-piece section 380 of FIG. 7 may be interconnected within the main flow conduit of breathable gas between flexible hoses 134, 152. The bottom branch of T-piece section 380 may be attached to bottom sections 382,383 to form an enclosed nebulizer chamber. Such connection means may be forced-fit, sliding-sleeve connections, or threaded connections, but preferably, the sections are permanently bonded or of one-piece construction to prevent separation accidents.

The hollow T-piece branch section includes an introduction path means 383 having a female luer-lock connector 384 for attaching a male luer-lock connector 386 of liquid medicine source 388 to direct the liquid medicine from the source, through connection 384, past one-way valve 390 and through tube 392 extending sufficiently toward the lower region 394 for delivering liquid medicine for storage in the lower region for a subsequent nebulizer treatment.

Another introduction path means may be included for introducing medical liquid from pressurized canister 400. Connector 402 of the canister attaches into the external end of the flow path at connector 404. The attendant applies force vertically downward to source 400 to seal the attachment between such connection means, and to activate the canister for discharging a dose of liquid medication. Liquid medicine flows from source 400, past valve means 406, out of nozzle 408 and into the nebulizer chamber. The internal pressure of source 400 nebulizes the medicine into particles of liquid and the nozzle projects the particles in a jet down the inspiratory flow-path toward the patient.

Valve 406 is shown as an axially-rotatable valve which unblocks the path means by utilizing wings 410 to rotate the inner sleeve 412 within fixed outer sleeve 414 to align jet nozzle 408 with aperture port 416 through the outer sleeve. Such path means are blocked by using the wings to rotate the inner sleeve so that the nozzle is not aligned with the port and the outer sleeve is a barrier to block flow. Alternatively, a stop-cock valve (not shown) could be used in a similar manner.

The T-piece section 380 also includes a liquid removal path means. Vacuum tube 420 of disposal means for liquid is forced to slide over a convex, tapered end of activating adaptor 422 to seal with the adaptor. The adaptor is positioned for sealed attachment with connector 423 utilizing a free-sliding fit with probe-activated valve 424. The tube/adaptor is pushed downward by constant force for sealing the attachment and to activate (to open) valve 424. The vacuum draws undesired liquid upward from the bottom of lower region 394, upward through tube 426, past valve 424, through activating adaptor 422 and into disposal tube 420.

Alternatively, vacuum tube .420 of disposal means may include a hollow activating-probe (not shown) which is forced to slide into activating adaptor 422 or activating adaptor 422 may be eliminated and such hollow probe forced to slide directly into the probe-activated valve to seal for vacuum removal of undesired liquid.

Elongated, flexible holder 428 connects between activating adaptor 422 and another part of the T-piece section 380 to orient the activating adaptor in position with valve 424 without normally activating the valve to provide for activating the valve only while the activating adaptor is pushed toward the valve by the attendant.

One or more caps may be provided for the ends of such servicing flow-paths to eliminate any leakage and prevent contamination as previously discussed for other embodiments of the invention.

Medical liquid may be introduced from source means for liquid medicine, through removal path means, as an alternative or in addition to providing introductory path means 383. During introduction of the liquid medicine through adaptor 422, residual medicine tends to remain in the adaptor 422 above valve 424, in the valve, and in tube 426. If required, a source of pressurized gas, such as a syringe, may be attached to the adaptor for pushing the liquid medicine down into the chamber lower region.

Alternately, a source of liquid medicine may be directly attached at the external end at connector 423. Either elongated holder 428 is made sufficiently flexible to allow detaching adaptor 422, or the adaptor may be eliminated. Residual medicine tends to remain in valve 424 and tube 426 but the medicine eventually works its way down the tube into the lower region due to the fluctuating pressure in the system.

Connector 423 may be provided with female luer-lock threads, as shown for connector 334 of FIG. 6, to attach a medicine source such as 388 with threaded male luer-lock connector 386. Such a source must have sufficient internal pressure to drive the liquid medicine through valve 424 and into the nebulizer chamber.

A source of medicine, automatically pressurized by ventilator system pressure fluctuations for discharging such liquid, may be provided. Such an automatically discharging source of liquid medicine may contain a reservoir for such liquid, and an exit flow-path for discharging the liquid from the bottom of the reservoir, through the exit flow-path and through a connector for sealed attachment to the external end of removal path means at connector 423.

Preferably, automatically discharging sources initially contain sufficient gas or the source is sufficiently flexible so that during the inspiratory phase, high system pressures force fluid up through the end of tube 426, through open valve 424 and into the reservoir of the medicine source means. During the lower pressure expiration phase, the recoil of the flexible reservoir, or the pressurized gas, discharges the liquid medicine from the bottom of the source reservoir, through valve 424, through tube 426 and into the chamber lower region. When the bottom of tube 426 is not covered with liquid during an inspiration phase, then the fluid which travels up the tube is pressurized gas. During the following expiration phase the pressurized gas in the reservoir pushes the liquid medicine out of the reservoir bottom, through removal path means and into the lower region for subsequent nebulization.

One-way valve 430 may be interconnected within the nebulizing-gas supply flow-pathway, as shown, to prevent fluctuating system pressures from conveying liquid from lower region 394 down into the nebulizing gas flow-pathway when nebulizing-gas is turned off at the ventilator.

Figure 8:
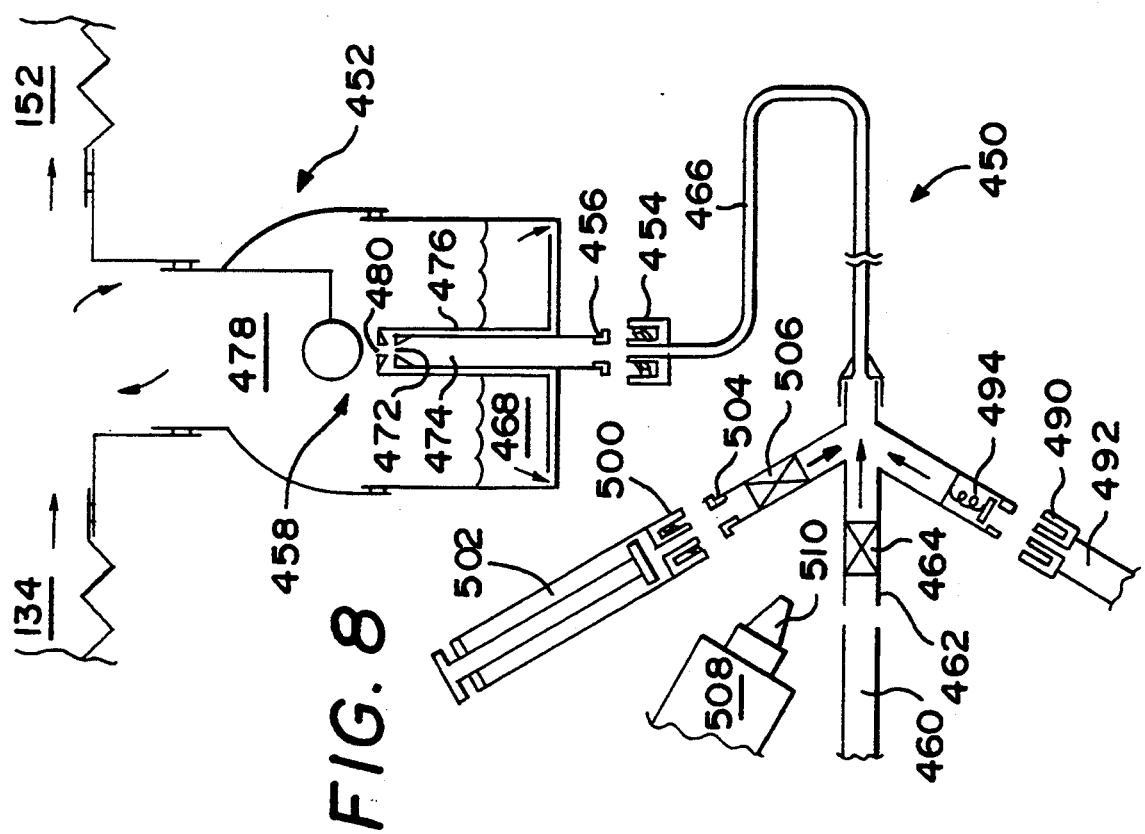
FIG. 8 schematically illustrates a medical apparatus embodiment of the invention for attaching to the nebulizing-gas nipple at the bottom of a conventional updraft nebulizer to remove undesired liquid from the nebulizer chamber, to introduce and store liquid medicine in the nebulizer chamber and to introduce nebulizing gas to the nebulizer for nebulizing the stored, liquid medicine.

Medical apparatus 450, for servicing updraft nebulizer component 452 in FIG. 8, may include a nebulizing-gas flow-pathway with connection means 454 for sealed attachment to nebulizing-gas nipple 456 at the bottom of nebulizer component 452. The connection may be a forced-fit connection, or preferably a luer-lock connection as shown to prevent disconnection accidents, or more preferably the connection is bonded and the nebulizer component and medical apparatus are provided as one-piece.

Source tube for pressurized nebulizing-gas 460 may be attached to seal with an external end at connection means 462 of the nebulizing-gas flow-pathway of the medical apparatus by forcing a flexible end of tube 460 to slide over the rounded end 462 of one-way valve 464. The nebulizing-gas flows from source tube 460, past valve 464, through flexible micro-tube 466, such as plastic intravenous tubing, through bottom nipple 456 and to nebulizer 458, shown as a gas-jet and baffle type nebulizer. Alternately nebulizer 534 may be an ultrasonic nebulizer means, thus, eliminating the need for nebulizing gas source 460, and valve 464.

Undesired liquid may be removed from lower region 468 of a conventional updraft nebulizer component by applying sufficient suction to nebulizing-gas nipple 456 located at the bottom of the nebulizer component. Sufficient suction applied to nipple 456 causes sufficient vacuum at the top end of jet nozzle aperture 472 through the top of the innermost tube 474, in order to draw liquid from lower region 468 up vacuum path means between innermost tube 474 and outermost tube 476 to the top of the innermost tube. The vacuum also draws gas from chamber upper region 478 down through orifice aperture 480, through the top of the outermost tube, to the top of the innermost tube. The gas and liquid mix and the mixture flows downward through nozzle 472, down the innermost tube and out of the nebulizer component through bottom nipple 456.

The medical apparatus includes a branch connection for liquid communication with the nebulizing gas flow-pathway for removing undesired liquid from lower region 468 of the nebulizer component. Activating-probe 490 of vacuum disposal means 492 may be periodically inserted into probe-activated valve 494 for a sufficient period for removing undesired liquid; and then the activating-probe is removed from valve 494 to prevent excessive removal of breathable gas which would reduce tidal volumes supplied to the patient and to prevent removal of liquid medicine introduced for the next nebulizer treatment.

The vacuum of disposal means 492 draws the undesired liquid out of the nebulizer component as previously described. The mixture of gas and undesired liquid flow from nipple 454, through micro-tube 466, past valve 494 and into disposal means 492.

Medicinal liquid may be introduced into the nebulizer component through the removal branch or through the nebulizing-gas flow-pathway depending on the type of source of liquid medicine. For example, a syringe with a luer-lock connector loaded with liquid medicine could be attached to valve 494. However, the specific embodiment of medical apparatus shown includes a separate branch connection and path means for introducing liquid medicine.

Male luer-lock connector 500 of source 502 for medicinal liquid may be periodically attached to female luer-lock connector 504 of medical apparatus for sealed introduction of liquid medicine from source 502, past one-way valve 506 and into the nebulizing-gas flow-pathway which delivers the liquid medicine into lower region 468 of the nebulizer component.

Liquid medicine may also be periodically introduced from pressurized canister 508 of liquid medicine by inserting the nipple 510 of the canister into female luer-lock connector 504. If immediate introduction of nebulized particles is desired, then the pressure in the canister is selected to provide nebulization during introduction. Any liquid which is not nebulized during introduction is deposited in the chamber lower region and nebulized, utilizing nebulizing-gas as previously described.

Caps and holders may be provided for connector 504 and the open end of valve 494, as previously discussed, for preventing leaks and contamination between periodic servicing.

Figure 9:
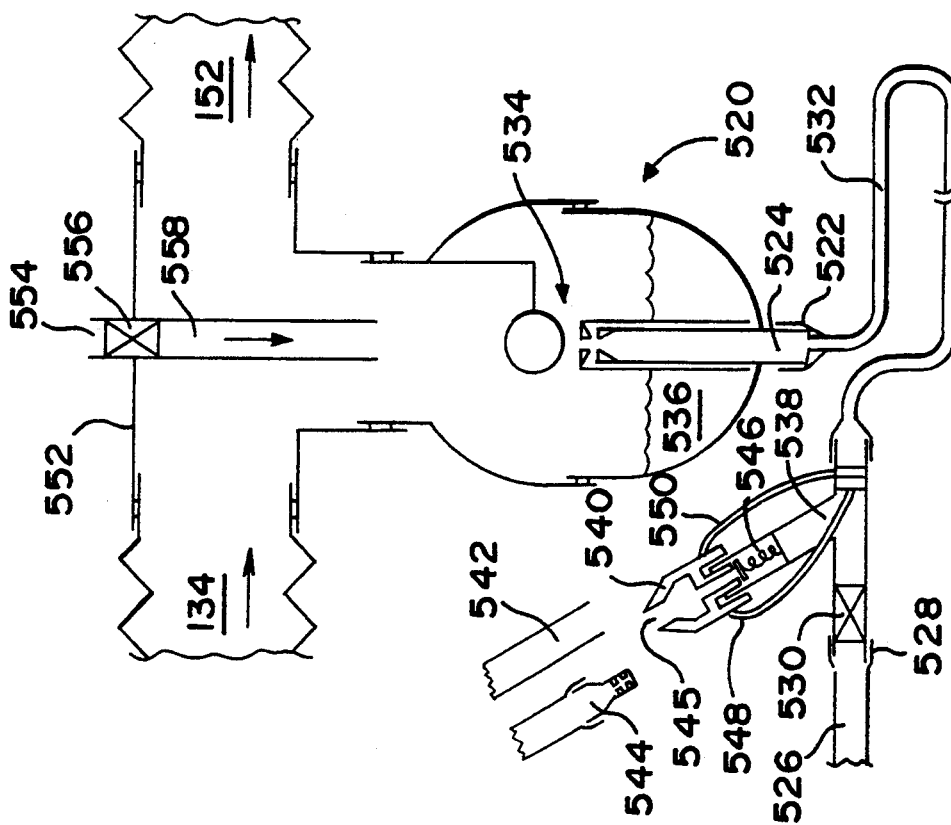

Medical apparatus for servicing nebulizer component 520 in FIG. 9 includes a shared flow-path with connection means 522 for attachment to nebulizing-gas nipple 524 at the bottom of the nebulizer component as shown. Flexible, nebulizing-gas, source tube 526 is forced to slide over the end of connection means 528 of one-way valve 530. Pressurized nebulizing-gas flows from the source, past valve 530, through flexible micro-tube 532, such as plastic intravenous tubing, through nipple 524 and to nebulizer 534.

Undesired liquid is removed from the bottom of lower region 536 through nipple 524, through micro-tube 532 of the shared flow-path and into branch connection 538 of removal path means. The medical apparatus removal path means includes activating adaptor 540 which may be attached to tube 542 of disposal means by forcing the tube to slide over the tapered end of the adaptor or may be attached to hollow probe 544 by forcing the end of the probe to insert into aperture 545 of the activating adaptor. The activating adaptor communicates with probe-activated valve 546 so that the valve opens when the probe of the adaptor (810 in FIG. 13) is pushed into the end of the probe-activated valve. Undesired liquid flows out of the shared flow-path through branch 538, past valve 546, through adaptor 540 and into tube 542 or probe 544 of disposal means.

Flexible elongated holders 548 and 550 connect at each diametrical side of adaptor 540 to orient the adaptor in position with the probe-activated valve. The tension of the connectors 548,550 is not sufficient to activate the valve or maintain the valve in an activated condition so that the valve is opened only while the attendant is pushing the adaptor into the valve.

Connectors 548, 550 are sufficiently flexible to allow adaptor 540 to be removed from valve 546 and held in proximity with the valve. This allows an activating-probe of a source of liquid medicine (not shown) to be inserted into valve 546 for introducing liquid through the valve, through micro-tube 532 and into the lower region 536.

More conveniently, the medical apparatus may include access means for adding liquid medicine through the top of T-piece section 552. A source of liquid medicine may be attached at connection means 554 for delivery past one-way valve means 556 and through path means 558 which directs the medicine into the lower region 536 of the nebulizer component for subsequent nebulization by the nebulizer.

In FIG. 10 removal path means of FIG. 9 has been modified by eliminating the elastic connectors 548,550 and adding sleeve means 570 to prevent leakage during the removal of undesired liquid or introduction of medicinal liquid through removal path means. Sleeve means 570 include a sleeve/skirt of elastic material attached to seal at 572 with activating adaptor 540 and attached to seal at 574 with probe-activated valve 546. Such sleeve means positions the activation adaptor to operate the valve, and is flexible to allow adaptor 540 to move axially relative to the valve to open/close the valve while preventing leakage into the surrounding ambient environment when the valve is opened.

Cap 576 may be attached to connector 540 when servicing means are not attached to the connector to eliminate the possibility of leakage through valve 546 into the surrounding ambient environment spreading contamination and to prevent contamination from entering the open external end of the path means. When servicing means are attached at the open end of adaptor 540, the cap is positioned proximate to the adaptor by elongated holder 578, to prevent contamination of the cap and to provide for convenient reattachment of the cap.

Another embodiment of the medical apparatus of FIG. 9 is presented in FIG. 11 in which an adaptor connection 522 at one end of micro-tube 532 may be attached to the nebulizing-gas nipple (not shown) at the bottom of an updraft nebulizer component and a female luer-lock connector 582, integral with probe-activated valve 580, provides for sealed attachment to means for servicing the nebulizer component. A male luer-lock connector 584 can be attached to connector 582 of the shared flow-path to open valve 580 for providing nebulizing-gas from nebulizing-gas source tube 586, past one-way valve 588, past probe-activated valve at 580, through tube 532 and into the attached nebulizer component. Activating-probe 600 of source 602 of liquid medicine may be pushed into connector 582 for sealed introduction of liquid medicine directed from source 602, past valve 580, and into the lower region of the attached nebulizer component. Activating-probe 610 of vacuum disposal means 612 for liquids may be pushed into connector 582 to open valve 580 for removal of undesired liquid from the lower region of the nebulizer component.

Nebulizer component 750 in FIG. 12 includes T-piece branch adaptor section 752 with horizontal arms terminating with connection means to provide for interconnection within the main conduit for breathable gas and a bottom connection means for attaching to interface section 754. The interface section has a flat top and a bottom connection means for attachment to cup-like section 756. The three sections attach to form an enclosed nebulizer chamber with a lower region 758 for periodically storing a dose of liquid medication and an upper region for mixing a fog of gas and nebulized particles of liquid medication with the breathable gas flowing through the inspiratory flow-path to the patient. The three sections may be attached using threaded or forced-fit sliding sleeve connections but preferably the three sections are permanently bonded or of one-piece construction.

Nebulizing-gas is introduced to nebulizer 760 from source tube 762 for nebulizing-gas which includes male luer-lock connector 764 for sealed attachment to female luer-lock connector 766 of shared flow-path 768. Nebulizing gas is introduced from source 762 through the flow-pathway, past one-way valve 770 and through the atomizer gas nozzle 772 of the nebulizer. The nebulizing gas source may be detached, as shown, and source means (not shown) may be attached to connector 766 for introducing liquid medicine, through the shared flow-path, past valve 770 and through nozzle 772 for storing the medical liquid in lower region 758 for subsequent nebulization.

Removal means (not shown) may be attached to valve 782 for removing undesired liquid from lower region 758, through tube 780, past probe-activated valve 782 and into removal means.

Adaptor 800 in FIG. 13 includes probe section 802 and tapered, hollow adaptor section 804. Probe section 802 is similar to a male luer-lock connector. Conventional probe-activated valve 806 provides for sealed connection and activation by such male luer-lock connectors. Section 802 includes external sleeve section 808 and hollow activating-probe 810. Tubular probe 810 is slightly smaller in diameter than conventional activating-probes, such as the probe of a standard luer-lock connector, and cylindrical sleeve 808 is concentric/-coaxial with probe 810 and has no threads. This configuration allows the adaptor to easily slip into and out of the end of the probe-activated valve without binding so that the spring of the probe-activated valve provides sufficient force to push the adaptor back for automatically deactivating the valve when the attendant is not applying force to push the adaptor into the valve. Such probe-activated valves are well known in the art.

The adaptor section has an exterior surface 812 in a convex, tapered configuration for sealed attachment to the flexible end of a tube (not shown) which may be forcibly slid over the exterior surface 812. The adaptor section also includes aperture 814 for sealed attachment to a conventional hollow activating-probe 816 for sealed fluid communication through such probe-activated valves. For probe-activated valves with luer-lock threads at the end (334 in FIG. 6) the internal diameter of sleeve 808 is increased to maintain clearance for providing a free-sliding fit. Conventional hollow activating-probes such as probe 816 are well known in the art.

Plastic materials and fabrication methods for medical devices are available and known in the art; and, specifics as to such materials and fabrication are not required by those skilled in the art for understanding and utilizing the invention. Specific selections of access means of the invention, as well as specific connection means, liquid flow path means, and valve means have been illustrated and described. While the advantages of these embodiments will be appreciated by those skilled in the art, other contributions do not depend upon these specific selections. For example, valves described as one-way valves could be replaced by manual two-way valves or, preferably, by two-way valves which are only active while an attendant is applying force/pressure (such as tube clamp, lever-activated, or push button valves) or more preferably, by two-way valves which automatically activate when attached to service means (such as probe-activated valves), but most preferably, the one-way valves which automatically activate only to allow sufficiently pressurized fluid to flow into the nebulizer chamber, as specified, are provided. Thus, while the invention has been particularly illustrated and described with reference to specific embodiments, it will be understood by those skilled in the art that changes in form and detail can depart from the specific embodiments without departing from the scope and spirit of the invention.

We claim:

1. A ventilator system of a type that delivers breathable gas to a patient at a selected system pressure and tidal volume comprising;
   a patient breathing tube having a first end for reception by the patient and a second end;
   a source of breathable gas;
   a conduit forming a flow path between said source of breathable gas and said second end;
   a source of nebulizing gas;
   a nebulizer housing disposed along said conduit having an upper chamber and a lower chamber and said upper chamber in combination with said flow path;
   said lower chamber forming a receptacle for medicine to be nebulized;
   said housing formed with first and second access openings;
   means for delivering medicine through said first access opening; means for delivering nebulizing gas from said source of nebulizing gas to said first access opening; and
   means for connecting alternatively, said first or second means to said first access opening.

2. The ventilator system of claim 1 wherein said first access opening is through said upper chamber.

3. The ventilator system of claim 1 wherein said second access opening is through said lower chamber, and means are provided for removing liquid from said lower chamber through said second access opening.

4. A ventilator system of a type that delivers breathable gas to a patient at a selected system pressure and tidal volume comprising:
   a patient breathing tube having a first end for reception by the patient and a second end;
   a source of breathable gas;
   a conduit forming a flow path between said source of breathable gas and said second end;
   a source of nebulizing gas;
   a nebulizer housing assembly disposed along said conduit having an upper chamber and a lower chamber and said upper chamber being in communication with said flow path;
   said lower chamber forming a receptacle for medicine to be nebulized;
   said housing formed with a plurality of access openings;
   a vacuum source;
   a fitting secured to one of said plurality of openings;
   said fitting having a first tubular branch and a second tubular branch;
   said first tubular branch leading to said source of nebulizing gas and said second tubular branch leading to said vacuum source; and
   means for connecting said second tubular branch to said vacuum source and for removing liquid from said lower chamber through said second branch.

5. The ventilator system of claim 4 wherein second tubular means are provided for delivering medicine to said lower chamber through a second opening of said plurality of openings.

6. The ventilator system of claim 5 wherein said second opening is through said upper chamber.

7. The ventilator system of claim 4 wherein a one-way valve is disposed in said first tubular branch and a second one-way valve is disposed in said second tubular branch.

8. A ventilator system of a type that delivers breathable gas to a patient at a selected system pressure and tidal volume comprising:
   a patient breathing tube having a first end received by the patient and second end;
   a source of breathable gas;
   a conduit forming a flow path between said source of breathable gas and said second end,
   a source of nebulizing gas,
   a nebulizer housing disposed along said conduit having an upper chamber and a lower chamber and said upper chamber being in communication with said flow path;
   said lower chamber forming a receptacle for medicine to be nebulized;
   said housing formed with first and second access openings;
   means for receiving, alternately, a medicine or a nebulizing gas through said first opening;
   second means for delivering a nebulized medicine carrying gas directly into said flow path; and
   third means for removing liquid from said lower chamber through said second opening.

9. The ventilator system of claim 8 wherein said means for delivering a nebulized medicine carrying gas into said flow path is a pressurized canister carrying medicine herein.

10. A ventilator system of a type that delivers breathable gas to a patient at a selected system pressure and tidal volume comprising:
- a patient breathing tube having a first end for reception by the patient and a second end;
- a source of breathable gas;
- a conduit forming a flow path between said source of breathable gas and said second end,
- a source of nebulizing gas,
- a nebulizer housing disposed along said conduit having an upper chamber and a lower chamber and said upper chamber in communication with said flow path;
- said lower chamber forming a receptacle for medicine to be nebulized;
- said housing formed with an access opening;
- means for introducing medicine through said access opening and to deposit said medicine in said lower chamber;
- means for delivering said nebulizing gas from said source of nebulizing gas to said lower chamber;
- a source of vacuum pressure; and
- means for removing liquid from said lower chamber through said access opening by connecting same access opening to said source of vacuum pressure.

11. A ventilator system of a type that delivers breathable gas to a patient at a selected system pressure and tidal volume comprising:
- a patient breathing tube having a first end for reception by the patient and a second end;
- a source of breathable gas;
- a conduit forming a flow path between said source of breathable gas and said second end,
- a source of nebulizing gas,
- a nebulizer housing disposed along said conduit having an upper chamber and a lower chamber and said upper chamber being in communication with said flow path;
- said lower chamber forming a receptacle for medicine to be nebulized;
- said housing formed with an access opening;
- a tubular fitting having one end received in said opening, and having a second end;
- first, second and third branches extending from said second end;
- said first branch receiving a supply of nebulizing gas;
- said second branch receiving a supply of medicine; and
- said third branch leading to a liquid disposal site.

12. The ventilator system of claim 11 wherein one way valves are disposed in said first and second branches.

* * * * *